United States Patent [19]

Jahn et al.

[11] Patent Number: 4,812,160
[45] Date of Patent: Mar. 14, 1989

[54] CYCLOHEXENONE DERIVATIVES, PREPARATION AND USE THEREOF AS HERBICIDES

[75] Inventors: Dieter Jahn, Edingen-Neckarhausen; Michael Keil, Freinsheim; Dieter Kolassa, Ludwigshafen; Ulrich Schirmer, Heidelberg; Bruno Wuerzer, Otterstadt; Norbert Meyer, Ladenburg; Johann Jung; Wilhelm Rademacher, both of Limburgerhof, all of Fed. Rep. of Germany

[73] Assignee: BASF Aktiengesellschaft, Ludwigshafen, Fed. Rep. of Germany

[21] Appl. No.: 946,060

[22] Filed: Dec. 24, 1986

[30] Foreign Application Priority Data

Jan. 11, 1986 [DE] Fed. Rep. of Germany ....... 3600642

[51] Int. Cl.$^4$ .................. A01N 43/16; C07D 309/02; C07D 311/02
[52] U.S. Cl. ........................................ 71/88; 549/387; 549/396; 549/417; 549/419; 549/420; 549/426; 549/427
[58] Field of Search ............... 549/387, 396, 416, 417, 549/419, 420, 423, 426, 427, 428; 71/88

[56] References Cited

U.S. PATENT DOCUMENTS

| 4,316,737 | 2/1982 | Guigues et al. | 549/396 X |
| 4,422,864 | 12/1983 | Becker et al. | 549/426 X |
| 4,596,877 | 6/1986 | Becker et al. | 71/90 |
| 4,602,935 | 7/1986 | Becker et al. | 549/419 X |
| 4,624,696 | 11/1986 | Keil et al. | 549/396 X |
| 4,668,275 | 5/1987 | Keil et al. | 549/396 X |

FOREIGN PATENT DOCUMENTS 0123001 10/1984 European Pat. Off. .
0126713 11/1984 European Pat. Off. .
0071707 12/1984 European Pat. Off. .

*Primary Examiner*—John W. Rollins, Jr.
*Assistant Examiner*—W. Catchpole
*Attorney, Agent, or Firm*—Keil & Weinkauf

[57] ABSTRACT

Cyclohexenone derivative of the formula where
A is oxygen or $NOR^8$, where $R^8$ is alkyl, alkenyl, alkynyl, haloalkyl or haloalkenyl, chlorothienyl or alkoxyalkyl
B is O, S, SO or $SO_2$,
X is hydrogen or methoxycarbonyl,
$R^1$ is hydrogen, carbonylalkyl, benzoyl or a cation,
$R^2$ is alkyl,
$R^3$ and $R^4$ are hydroxyl, chlorine, bromine, thioalkylcarboxyl, thiocarbonylalkyl, alkylcarbonyloxy, alkoxy, or alkylthio, or $R^3$ and $R^4$ together epoxy,
$R^5$ and $R^6$ are hydrogen or methyl or $R^5$ and $R^6$ are together methyleneoxyethylene, and
$R^7$ is hydrogen or methyl, and herbicides containing these compounds.

6 Claims, No Drawings

CYCLOHEXENONE DERIVATIVES, PREPARATION AND USE THEREOF AS HERBICIDES

The present invention relates to novel cyclohexanone derivatives having a herbicidal action, to agents based on such cyclohexanone derivatives, and to processes for their preparation and use as herbicides.

The herbicidal action of oxime ethers having a cyclohexenone structure and nonaromatic substituents in the 5-position is known from EP No. 71,707.

It is further known that certain 2-acyl-3-hydroxycyclohex-2-en-1-ones regulate plant growth (EP No. 123,001 and EP No. 126,713).

We have found that cyclohexenone derivatives of the formula

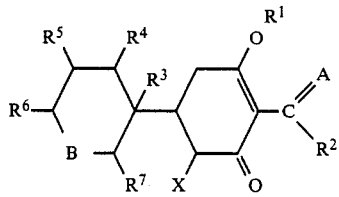

where
A is oxygen or $NOR^8$, where $R^8$ is alkyl of 1 to 4 carbon atoms, alkenyl of 3 or 4 carbon atoms, alkynyl of 3 or 4 carbon atoms, haloalkyl or haloalkenyl of 2 to 4 carbon atoms and 1 to 3 halogen atoms, chlorothienyl or alkoxyalkyl of 2 to 4 carbon atoms,
B is O, S, SO or $SO_2$,
X is hydrogen or methoxycarbonyl,
$R^1$ is hydrogen, carbonylalkyl of 2 to 18 carbon atoms or benzoyl or an inorganic or organic cation,
$R^2$ is alkyl of up to 4 carbon atoms,
$R^3$ and $R^4$, independently of each other, are each hydroxyl, chlorine, bromine, thioalkylcarboxyl, thiocarbonylalkyl, alkylcarbonyloxy each of up to 4 carbon atoms or $R^3$ and $R^4$ are together alkoxy of up to 3 carbon atoms and hydroxyl or together alkylthio of up to 3 carbon atoms and hydroxyl or together epoxy,
$R^5$ and $R^6$, independently of each other, are each hydrogen or methyl or $R^5$ and $R^6$ are together methyleneoxyethylene,
$R^7$ is hydrogen or methyl,
have a powerful herbicidal action, preferably on species of the family of the grasses (Gramineae). They are compatible and thus selective in broad-leaf crops and also in monocotyledons which do not belong to the Gramineae. In addition, numerous compounds are also selective in Gramineae crops such as wheat and rice and at the same time control undesirable grasses. They are biologically superior to comparable compounds.

Examples of $R^1$ in the formula I are: hydrogen, acetyl, propionyl, butyryl, pivaloyl, palmitoyl, stearoyl, benzoyl, sodium, potassium, ammonium, calcium, magnesium, trialkylammonium, tetraalkylammonium, trialkylbenzylammonium, trialkylsulfonium and trialkylsulfoxonium.

Examples of $R^2$ in the formula I are: methyl, ethyl, n-propyl, i-propyl, n-butyl and i-butyl.

Examples of $R^3$ and $R^4$ are: alkoxy such as methoxy, ethoxy, n-propoxy or i-propoxy, alkylthio such as methylthio, ethylthio or n-propylthio, hydroxyl, bromine, chlorine, thioalkylcarboxyl such as thiomethylcarboxyl or thioethylcarboxyl, thiocarbonylalkyl such as thiocarbonylmethyl or thiocarbonylethyl, dimethylamino, acetoxy, propionyloxy, butyryloxy and epoxy.

Examples of $R^8$ are: methyl, ethyl, n-propyl, i-propyl, allyl, (E)-2-butenyl, 2-fluoroeth-1-yl, 2-chloroeth-1-yl, (E)-3-chloro-2-propenyl, 1,1,2-trichloroprop-1-en-3-yl, chlorothienyl, propargyl, methoxymethyl and methoxyethyl.

The cyclohexenone derivatives of the formula I where A is $NOR^8$ and $R^1$ is hydrogen can be obtained by reacting compounds of the formula

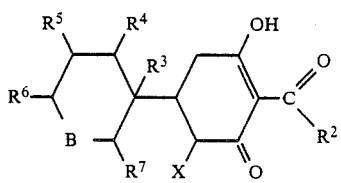

where $R^2$, $R^3$, $R^4$, $R^5$, $R^6$, $R^7$ and X have the abovementioned meanings, with alkoxyammonium compounds of the formula $R^8 ONH_3Y$, where Y is an anion. To this end the two reactants are reacted with each other, for example in a solvent in the presence of a base at from 0° C. to the boiling point of the solvent. Suitable bases are for example carbonates, hydrogencarbonates, acetates, alcoholates, oxides or hydroxides of alkali and alkaline earth metals, in particular sodium, potassium, magnesium or calcium, or organic bases, such as pyridine or tertiary amines.

Suitable solvents are for example dimethyl sulfoxide, alcohols such as methanol, ethanol or isopropanol, benzene, toluene, hydrocarbons and chlorohydrocarbons, such as chloroform, dichloroethane, hexane or cyclohexane, esters, such as ethyl acetate, or ethers, such as dioxane or tetrahydrofuran.

The reaction is complete within a few hours, and the reaction product can be isolated by concentrating the mixture, partitioning the residue between methylene chloride and water and distilling off the solvent under reduced pressure.

The compounds of the formula I where A is $NOR^8$ and $R^1$ is hydrogen can also be obtained by reacting the compounds of the formula I where A is oxygen and $R^1$ is hydrogen with appropriate alkoxyamines of the formula $R^8$—$ONH_2$ in a suitable diluent; suitable reaction temperatures range in general from 15° to 70° C. The alkoxyamine can be used in the form of an aqueous solution; depending on the solvent used for the other reactant, a one- or two-phase reaction mixture is obtained.

Suitable solvents for the reaction are for example alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

Alkali metal salts of compounds I can be obtained by treating the compounds with alkaline compounds such as sodium hydroxide, potassium hydroxide, sodium alcoholate or potassium alcoholate in aqueous solution or in an organic solvent, such as methanol, ethanol, acetone or toluene.

Other metal salts, for example the managanese, copper, zinc, iron, calcium, magnesium and barium salts, can be prepared from the sodium salts in a conventional manner (by reaction with salts of the metals with inorganic acids), as in the same way the ammonium and phosphonium salts can be prepared by means of ammonia or phosphonium, sulfonium or sulfoxonium hydroxides.

The compounds of the formula I where A is oxygen can be prepared, for example from the corresponding cyclohexane-1,3-diones II

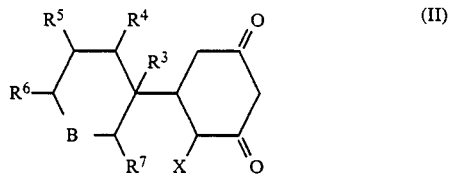

by literature methods (*Tetrahedron Lett.* 29, (1975), 2491).

It is also possible to prepare compounds of the formula I where A is oxygen via the enol ester intermediate obtained on reacting compounds of the formula II with acid chlorides in the presence of bases and subsequently rearranged with certain imidazole or pyridine derivatives (Japanese Preliminary Published Application No. 79/063,052).

The compounds of the formula II can be obtained by literature methods as given for example in German Laid-Open Application DOS No. 3,219,490.

It is also possible to introduce the substituents $R^3$ and $R^4$ at a later stage, preferably directly into compounds of the formula I where A is oxygen.

Suitable precursors are compounds of the formula

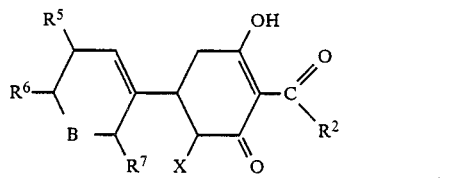

where literature reactions can be carried out on the double bond, for example addition of halogens, hydrogen halides, mercaptans, thiolcarboxylic acids, mercaptocarboxylic acids or epoxidation.

The epoxy derivatives thus obtained can serve as starting materials for further syntheses based on opening the oxirane ring, for example reaction with mercaptans, water or alcohols with or without acid or base catalysis.

The compounds of the formula I where B is SO or $SO_2$ can also be obtained by oxidizing appropriate precursors where the sulfur is in a lower state of oxidation. Oxidizing agents are for example oxygen, ozone, peroxy compounds, such as hydrogen peroxides, per-acids, hydroperoxides, halogens, inorganic halogen compounds, such as hypochlorite, chlorate, nitrogen compounds, such as nitric acid and dinitrogen pentoxide, or salts of metals of higher valence, such as lead, bismuth, vanadium, manganese, chromium or cobalt salts. Anodic oxidation is also possible. The oxidation can be carried out not only at the final stage but, in principle, at any stage of the synthesis route described above.

The examples which follow illustrate the preparation of the novel compounds. Parts by weight relate to parts by volume as the kilogram relates to the liter.

EXAMPLE 1

14.8 parts by weight of 2-propionyl-5-(5,6-dihydro-2H-pyran-3-yl)-3-hydroxy-2-cyclohexen-1-one are dissolved in 100 parts by volume of dichloromethane, and m-chloroperbenzoic acid is added at room temperature, and the reaction is monitored by means of thin layer chromatography. After the reaction has ended, the precipitated m-chlorobenzoic acid is filtered off, the filtrate is washed twice with semiconcentrated sodium bicarbonate solution and water and dried over sodium sulfate, and the solvent is distilled off under reduced pressure to leave 2-propionyl-5-(3,4-epoxy-tetrahydropyran-3-yl)-3-hydroxy-2-cyclohexen-1-one (compound No. 30).

EXAMPLE 2

3.0 parts by weight of 2-propionyl-5-(3,4-epoxy-tetrahydropyran-3-yl)-3-hydroxy-2-cyclohex-1-one, 1.8 parts by weight of (E)-3-chloro-2-propenyloxyammonium chloride, 1.1 parts by weight of sodium bicarbonate and 100 parts by volume of methanol are stirred at room temperature for 16 hours. The solvent is distilled off under reduced pressure, 50 parts by volume of water and 50 parts by volume of dichloromethane are added to the residue, after vigorous stirring the phases are separated, and the organic phase is dried over sodium sulfate. Distilling off the solvent under reduced pressure leaves 2-[1-((E)-3-chloro-2-propenyloxyimino)propyl]-5-(3,4-epoxy-tetrahydropyran-3-yl)-3-hydroxy-2-cyclohexen-1-one (compound No. 401).

The following compounds can be obtained in a similar manner:

(The $^1$H-NMR data are given in $\delta$ (ppm) and relate to tetramethylsilane as internal standard. Abbreviations: s=singlet, d=dublet, m=multiplet, q=quartet).

TABLE 1

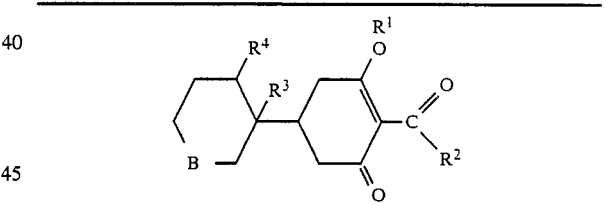

| No. | $R^1$ | $R^2$ | $R^3$ and $R^4$ | B | $^1$H—NMR data |
|---|---|---|---|---|---|
| 1 | H | Methyl | Cl | S | |
| 2 | H | Methyl | Cl | O | |
| 3 | H | Methyl | Cl | SO | |
| 4 | H | Methyl | Cl | $SO_2$ | |
| 5 | H | Methyl | Br | S | |
| 6 | H | Methyl | Br | O | |
| 7 | H | Methyl | Br | SO | |
| 8 | H | Methyl | Br | $SO_2$ | |
| 9 | H | Methyl | OH | S | |
| 10 | H | Methyl | OH | O | |
| 11 | H | Methyl | OH | SO | |
| 12 | H | Methyl | OH | $SO_2$ | |
| 13 | H | Methyl | Epoxy | S | |
| 14 | H | Methyl | Epoxy | O | |
| 15 | H | Methyl | Epoxy | SO | |
| 16 | H | Methyl | Epoxy | $SO_2$ | |
| 17 | H | Ethyl | Cl | S | |
| 18 | H | Ethyl | Cl | O | |
| 19 | H | Ethyl | Cl | SO | |
| 20 | H | Ethyl | Cl | $SO_2$ | |
| 21 | H | Ethyl | Br | S | |
| 22 | H | Ethyl | Br | O | |
| 23 | H | Ethyl | Br | SO | |
| 24 | H | Ethyl | Br | $SO_2$ | |
| 25 | H | Ethyl | OH | S | |

TABLE 1-continued

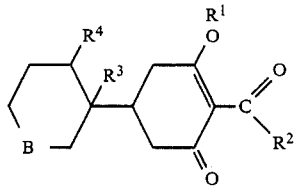

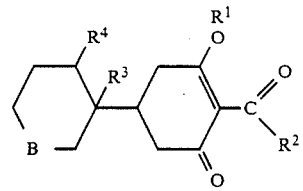

| No. | R¹ | R² | R³ and R⁴ | B | ¹H—NMR data |
|---|---|---|---|---|---|
| 26 | H | Ethyl | OH | O | |
| 27 | H | Ethyl | OH | SO | |
| 28 | H | Ethyl | OH | SO₂ | |
| 29 | H | Ethyl | Epoxy | S | |
| 30 | H | Ethyl | Epoxy | O | |
| 31 | H | Ethyl | Epoxy | SO | |
| 32 | H | Ethyl | Epoxy | SO₂ | |
| 33 | H | n-Propyl | Cl | S | |
| 34 | H | n-Propyl | Cl | O | 1.0(t), 3.9(m), 4.4(m) |
| 35 | H | n-Propyl | Cl | SO | |
| 36 | H | n-Propyl | Cl | SO₂ | |
| 37 | H | n-Propyl | Br | S | |
| 38 | H | n-Propyl | Br | O | 2.0(d), 3.0(m), 4.6(s) |
| 39 | H | n-Propyl | Br | SO | |
| 40 | H | n-Propyl | Br | SO₂ | |
| 41 | H | n-Propyl | OH | S | |
| 42 | H | n-Propyl | OH | O | 1.0(t), 1.6(q), 3.8(m) |
| 43 | H | n-Propyl | OH | SO | |
| 44 | H | n-Propyl | OH | SO₂ | |
| 45 | H | n-Propyl | Epoxy | S | |
| 46 | H | n-Propyl | Epoxy | O | |
| 47 | H | n-Propyl | Epoxy | SO | |
| 48 | H | n-Propyl | Epoxy | SO₂ | |
| 49 | H | n-Butyl | Cl | S | |
| 50 | H | n-Butyl | Cl | O | |
| 51 | H | n-Butyl | Cl | SO | |
| 52 | H | n-Butyl | Cl | SO₂ | |
| 53 | H | n-Butyl | Br | S | |
| 54 | H | n-Butyl | Br | O | |
| 55 | H | n-Butyl | Br | SO | |
| 56 | H | n-Butyl | Br | SO₂ | |
| 57 | H | n-Butyl | OH | S | |
| 58 | H | n-Butyl | OH | O | |
| 59 | H | n-Butyl | OH | SO | |
| 60 | H | n-Butyl | OH | SO₂ | |
| 61 | H | n-Butyl | Epoxy | S | |
| 62 | H | n-Butyl | Epoxy | O | |
| 63 | H | n-Butyl | Epoxy | SO | |
| 64 | H | n-Butyl | Epoxy | SO₂ | |
| 65 | Na⁺ | Methyl | Cl | S | |
| 66 | Na⁺ | Methyl | Cl | O | |
| 67 | Na⁺ | Methyl | Cl | SO | |
| 68 | Na⁺ | Methyl | Cl | SO₂ | |
| 69 | Na⁺ | Methyl | Br | S | |
| 70 | Na⁺ | Methyl | Br | O | |
| 71 | Na⁺ | Methyl | Br | SO | |
| 72 | Na⁺ | Methyl | Br | SO₂ | |
| 73 | Na⁺ | Methyl | OH | S | |
| 74 | Na⁺ | Methyl | OH | O | |
| 75 | Na⁺ | Methyl | OH | SO | |
| 76 | Na⁺ | Methyl | OH | SO₂ | |
| 77 | Na⁺ | Methyl | Epoxy | S | |
| 78 | Na⁺ | Methyl | Epoxy | O | |
| 79 | Na⁺ | Methyl | Epoxy | SO | |
| 80 | Na⁺ | Methyl | Epoxy | SO₂ | |
| 81 | Na⁺ | Ethyl | Cl | S | |
| 82 | Na⁺ | Ethyl | Cl | O | |
| 83 | Na⁺ | Ethyl | Cl | SO | |
| 84 | Na⁺ | Ethyl | Cl | SO₂ | |
| 85 | Na⁺ | Ethyl | Br | S | |
| 86 | Na⁺ | Ethyl | Br | O | |
| 87 | Na⁺ | Ethyl | Br | SO | |
| 88 | Na⁺ | Ethyl | Br | SO₂ | |
| 89 | Na⁺ | Ethyl | OH | S | |
| 90 | Na⁺ | Ethyl | OH | O | |
| 91 | Na⁺ | Ethyl | OH | SO | |
| 92 | Na⁺ | Ethyl | OH | SO₂ | |
| 93 | Na⁺ | Ethyl | Epoxy | S | |
| 94 | Na⁺ | Ethyl | Epoxy | O | |
| 95 | Na⁺ | Ethyl | Epoxy | SO | |
| 96 | Na⁺ | Ethyl | Epoxy | SO₂ | |
| 97 | Na⁺ | n-Propyl | Cl | S | |
| 98 | Na⁺ | n-Propyl | Cl | O | |
| 99 | Na⁺ | n-Propyl | Cl | SO | |
| 100 | Na⁺ | n-Propyl | Cl | SO₂ | |
| 101 | Na⁺ | n-Propyl | Br | S | |
| 102 | Na⁺ | n-Propyl | Br | O | |
| 103 | Na⁺ | n-Propyl | Br | SO | |
| 104 | Na⁺ | n-Propyl | Br | SO₂ | |
| 105 | Na⁺ | n-Propyl | OH | S | |
| 106 | Na⁺ | n-Propyl | OH | O | |
| 107 | Na⁺ | n-Propyl | OH | SO | |
| 108 | Na⁺ | n-Propyl | OH | SO₂ | |
| 109 | Na⁺ | n-Propyl | Epoxy | S | |
| 110 | Na⁺ | n-Propyl | Epoxy | O | |
| 111 | Na⁺ | n-Propyl | Epoxy | SO | |
| 112 | Na⁺ | n-Propyl | Epoxy | SO₂ | |
| 113 | Na⁺ | n-Butyl | Cl | S | |
| 114 | Na⁺ | n-Butyl | Cl | O | |
| 115 | Na⁺ | n-Butyl | Cl | SO | |
| 116 | Na⁺ | n-Butyl | Cl | SO₂ | |
| 117 | Na⁺ | n-Butyl | Br | S | |
| 118 | Na⁺ | n-Butyl | Br | O | |
| 119 | Na⁺ | n-Butyl | Br | SO | |
| 120 | Na⁺ | n-Butyl | Br | SO₂ | |
| 121 | Na⁺ | n-Butyl | OH | S | |
| 122 | Na⁺ | n-Butyl | OH | O | |
| 123 | Na⁺ | n-Butyl | OH | SO | |
| 124 | Na⁺ | n-Butyl | OH | SO₂ | |
| 125 | Na⁺ | n-Butyl | Epoxy | S | |
| 126 | Na⁺ | n-Butyl | Epoxy | O | |
| 127 | Na⁺ | n-Butyl | Epoxy | SO | |
| 128 | Na⁺ | n-Butyl | Epoxy | SO₂ | |
| 129 | K⁺ | Methyl | Cl | S | |
| 130 | K⁺ | Methyl | Cl | O | |
| 131 | K⁺ | Methyl | Cl | SO | |
| 132 | K⁺ | Methyl | Cl | SO₂ | |
| 133 | K⁺ | Methyl | Br | S | |
| 134 | K⁺ | Methyl | Br | O | |
| 135 | K⁺ | Methyl | Br | SO | |
| 136 | K⁺ | Methyl | Br | SO₂ | |
| 137 | K⁺ | Methyl | OH | S | |
| 138 | K⁺ | Methyl | OH | O | |
| 139 | K⁺ | Methyl | OH | SO | |
| 140 | K⁺ | Methyl | OH | SO₂ | |
| 141 | K⁺ | Methyl | Epoxy | S | |
| 142 | K⁺ | Methyl | Epoxy | O | |
| 143 | K⁺ | Methyl | Epoxy | SO | |
| 144 | K⁺ | Methyl | Epoxy | SO₂ | |
| 145 | K⁺ | Ethyl | Cl | S | |
| 146 | K⁺ | Ethyl | Cl | O | |
| 147 | K⁺ | Ethyl | Cl | SO | |
| 148 | K⁺ | Ethyl | Cl | SO₂ | |
| 149 | K⁺ | Ethyl | Br | S | |
| 150 | K⁺ | Ethyl | Br | O | |
| 151 | K⁺ | Ethyl | Br | SO | |
| 152 | K⁺ | Ethyl | Br | SO₂ | |
| 153 | K⁺ | Ethyl | OH | S | |
| 154 | K⁺ | Ethyl | OH | O | |
| 155 | K⁺ | Ethyl | OH | SO | |
| 156 | K⁺ | Ethyl | OH | SO₂ | |
| 157 | K⁺ | Ethyl | Epoxy | S | |
| 158 | K⁺ | Ethyl | Epoxy | O | |
| 159 | K⁺ | Ethyl | Epoxy | SO | |
| 160 | K⁺ | Ethyl | Epoxy | SO₂ | |
| 161 | K⁺ | n-Propyl | Cl | S | |
| 162 | K⁺ | n-Propyl | Cl | O | |
| 163 | K⁺ | n-Propyl | Cl | SO | |
| 164 | K⁺ | n-Propyl | Cl | SO₂ | |
| 165 | K⁺ | n-Propyl | Br | S | |

TABLE 1-continued

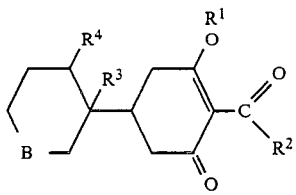

| No. | R¹ | R² | R³ and R⁴ | B | ¹H—NMR data |
|---|---|---|---|---|---|
| 166 | K⁺ | n-Propyl | Br | O | |
| 167 | K⁺ | n-Propyl | Br | SO | |
| 168 | K⁺ | n-Propyl | Br | $SO_2$ | |
| 169 | K⁺ | n-Propyl | OH | S | |
| 170 | K⁺ | n-Propyl | OH | O | |
| 171 | K⁺ | n-Propyl | OH | SO | |
| 172 | K⁺ | n-Propyl | OH | $SO_2$ | |
| 173 | K⁺ | n-Propyl | Epoxy | S | |
| 174 | K⁺ | n-Propyl | Epoxy | O | |
| 175 | K⁺ | n-Propyl | Epoxy | SO | |
| 176 | K⁺ | n-Propyl | Epoxy | $SO_2$ | |
| 177 | K⁺ | n-Butyl | Cl | S | |
| 178 | K⁺ | n-Butyl | Cl | O | |
| 179 | K⁺ | n-Butyl | Cl | SO | |

TABLE 1-continued

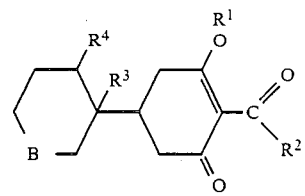

| No. | R¹ | R² | R³ and R⁴ | B | ¹H—NMR data |
|---|---|---|---|---|---|
| 180 | K⁺ | n-Butyl | Cl | $SO_2$ | |
| 181 | K⁺ | n-Butyl | Br | S | |
| 182 | K⁺ | n-Butyl | Br | O | |
| 183 | K⁺ | n-Butyl | Br | SO | |
| 184 | K⁺ | n-Butyl | Br | $SO_2$ | |
| 185 | K⁺ | n-Butyl | OH | S | |
| 186 | K⁺ | n-Butyl | OH | O | |
| 187 | K⁺ | n-Butyl | OH | SO | |
| 188 | K⁺ | n-Butyl | OH | $SO_2$ | |
| 189 | K⁺ | n-Butyl | Epoxy | S | |
| 190 | K⁺ | n-Butyl | Epoxy | O | |
| 191 | K⁺ | n-Butyl | Epoxy | SO | |
| 192 | K⁺ | n-Butyl | Epoxy | $SO_2$ | |

TABLE 2

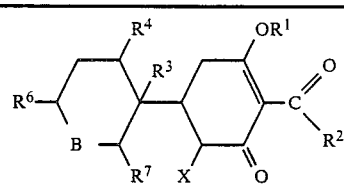

| No. | R¹ | R² | R³ and R⁴ | R⁶ | R⁷ | B | X | ¹H—NMR data |
|---|---|---|---|---|---|---|---|---|
| 193 | H | Ethyl | Epoxy | H | H | O | $COOCH_3$ | |
| 194 | H | Ethyl | Cl | H | H | O | $COOCH_3$ | |
| 195 | Trimethylbenzylammonium | n-Propyl | Epoxy | H | H | O | H | |
| 196 | H | n-Propyl | Epoxy | Methyl | Methyl | O | H | |
| 197 | H | n-Propyl | Cl | H | H | O | $COOCH_3$ | |
| 198 | H | n-Propyl | Br | H | H | O | $COOCH_3$ | |

TABLE 3

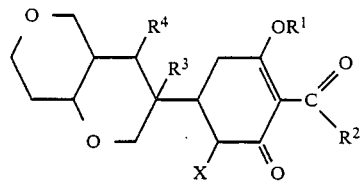

| No. | R¹ | R² | R³ and R⁴ | X | ¹H—NMR data |
|---|---|---|---|---|---|
| 199 | H | Methyl | Cl | H | |
| 200 | H | Methyl | Br | H | |
| 201 | H | Methyl | OH | H | |
| 202 | H | Methyl | Epoxy | H | |
| 203 | H | Ethyl | Cl | H | |
| 204 | H | Ethyl | Br | H | |
| 205 | H | Ethyl | OH | H | |
| 206 | H | Ethyl | Epoxy | H | |
| 207 | H | n-Propyl | Cl | H | |
| 208 | H | n-Propyl | Br | H | 1.0(t), 1.7(q), 4.0(s) |
| 209 | H | n-Propyl | OH | H | |
| 210 | H | n-Propyl | Epoxy | H | 1.0(t), 2.5(m), 4.1(m) |
| 211 | H | n-Butyl | Cl | H | |
| 212 | H | n-Butyl | Br | H | |
| 213 | H | n-Butyl | OH | H | |
| 214 | H | n-Butyl | Epoxy | H | |
| 215 | Na⁺ | Methyl | Cl | H | |
| 216 | Na⁺ | Methyl | Br | H | |
| 217 | Na⁺ | Methyl | OH | H | |
| 218 | Na⁺ | Methyl | Epoxy | H | |
| 219 | Na⁺ | Ethyl | Cl | H | |
| 220 | Na⁺ | Ethyl | Br | H | |

TABLE 3-continued

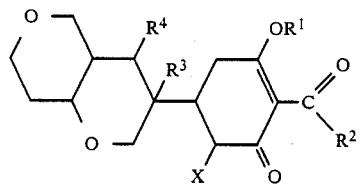

| No. | R¹ | R² | R³ and R⁴ | X | ¹H—NMR data |
|-----|----|----|-----------|---|-------------|
| 221 | Na⁺ | Ethyl | OH | H | |
| 222 | Na⁺ | Ethyl | Epoxy | H | |
| 223 | Na⁺ | n-Propyl | Cl | H | |
| 224 | Na⁺ | n-Propyl | Br | H | |
| 225 | Na⁺ | n-Propyl | OH | H | |
| 226 | Na⁺ | n-Propyl | Epoxy | H | |
| 227 | Na⁺ | n-Butyl | Cl | H | |
| 228 | Na⁺ | n-Butyl | Br | H | |
| 229 | Na⁺ | n-Butyl | OH | H | |
| 230 | Na⁺ | n-Butyl | Epoxy | H | |
| 231 | K⁺ | Methyl | Cl | H | |
| 232 | K⁺ | Methyl | Br | H | |
| 233 | K⁺ | Methyl | OH | H | |
| 234 | K⁺ | Methyl | Epoxy | H | |
| 235 | K⁺ | Ethyl | Cl | H | |
| 236 | K⁺ | Ethyl | Br | H | |
| 237 | K⁺ | Ethyl | OH | H | |
| 238 | K⁺ | Ethyl | Epoxy | H | |
| 239 | K⁺ | n-Propyl | Cl | H | |
| 240 | K⁺ | n-Propyl | Br | H | |
| 241 | K⁺ | n-Propyl | OH | H | |
| 242 | K⁺ | n-Propyl | Epoxy | H | |
| 243 | K⁺ | n-Butyl | Cl | H | |
| 244 | K⁺ | n-Butyl | Br | H | |
| 245 | K⁺ | n-Butyl | OH | H | |
| 246 | K⁺ | n-Butyl | Epoxy | H | |
| 247 | H | n-Propyl | Cl | COOCH₃ | |
| 248 | H | Ethyl | Cl | COOCH₃ | |
| 249 | Trimethylbenzylammonium | Ethyl | Cl | H | |
| 250 | Trimethylbenzylammonium | n-Propyl | Cl | H | |
| 251 | Tetramethylammonium | Ethyl | Epoxy | H | |
| 252 | Tetramethylammonium | Ethyl | Cl | COOCH₃ | |

TABLE 4

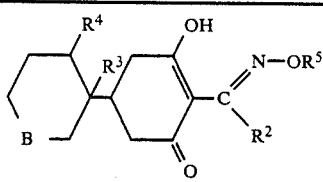

| No. | R² | R³ and R⁴ | B | R⁵ | ¹H—NMR data |
|-----|----|-----------|----|----|-------------|
| 253 | Methyl | Cl | S | Ethyl | |
| 254 | Methyl | Cl | S | Allyl | 50 |
| 255 | Methyl | Cl | S | (E)—2-Butenyl | |
| 256 | Methyl | Cl | S | (E)—3-Chloro—2-propenyl | |
| 257 | Methyl | Cl | S | Propargyl | |
| 258 | Methyl | Cl | O | Ethyl | |
| 259 | Methyl | Cl | O | Allyl | |
| 260 | Methyl | Cl | O | (E)—2-Butenyl | 55 |
| 261 | Methyl | Cl | O | (E)—3-Chloro—2-propenyl | |
| 262 | Methyl | Cl | O | Propargyl | |
| 263 | Methyl | Cl | SO | Ethyl | |
| 264 | Methyl | Cl | SO | Allyl | |
| 265 | Methyl | Cl | SO | (E)—2-Butenyl | |
| 266 | Methyl | Cl | SO | (E)—3-Chloro—2-propenyl | 60 |
| 267 | Methyl | Cl | SO | Propargyl | |
| 268 | Methyl | Cl | SO₂ | Ethyl | |
| 269 | Methyl | Cl | SO₂ | Allyl | |
| 270 | Methyl | Cl | SO₂ | (E)—2-Butenyl | |
| 271 | Methyl | Cl | SO₂ | (E)—3-Chloro—2-propenyl | |
| 272 | Methyl | Cl | SO₂ | Propargyl | 65 |
| 273 | Methyl | Br | S | Ethyl | |
| 274 | Methyl | Br | S | Allyl | |
| 275 | Methyl | Br | S | (E)—2-Butenyl | |
| 276 | Methyl | Br | S | (E)—3-Chloro—2-propenyl | |

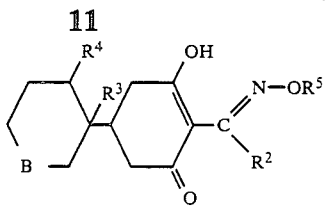

| No. | $R^2$ | $R^3$ and $R^4$ | B | $R^5$ | $^1$H—NMR data |
|---|---|---|---|---|---|
| 277 | Methyl | Br | S | Propargyl | |
| 278 | Methyl | Br | O | Ethyl | |
| 279 | Methyl | Br | O | Allyl | |
| 280 | Methyl | Br | O | (E)—2-Butenyl | |
| 281 | Methyl | Br | O | (E)—3-Chloro—2-propenyl | |
| 282 | Methyl | Br | O | Propargyl | |
| 283 | Methyl | Br | SO | Ethyl | |
| 284 | Methyl | Br | SO | Allyl | |
| 285 | Methyl | Br | SO | (E)—2-Butenyl | |
| 286 | Methyl | Br | SO | (E)—3-Chloro—2-propenyl | |
| 287 | Methyl | Br | SO | Propargyl | |
| 288 | Methyl | Br | $SO_2$ | Ethyl | |
| 289 | Methyl | Br | $SO_2$ | Allyl | |
| 290 | Methyl | Br | $SO_2$ | (E)—2-Butenyl | |
| 291 | Methyl | Br | $SO_2$ | (E)—3-Chloro—2-propenyl | |
| 292 | Methyl | Br | $SO_2$ | Propargyl | |
| 293 | Methyl | OH | S | Ethyl | |
| 294 | Methyl | OH | S | Allyl | |
| 295 | Methyl | OH | S | (E)—2-Butenyl | |
| 296 | Methyl | OH | S | (E)—3-Chloro—2-propenyl | |
| 297 | Methyl | OH | S | Propargyl | |
| 298 | Methyl | OH | O | Ethyl | |
| 299 | Methyl | OH | O | Allyl | |
| 300 | Methyl | OH | O | (E)—2-Butenyl | |
| 301 | Methyl | OH | O | (E)—3-Chloro—2-propenyl | |
| 302 | Methyl | OH | O | Propargyl | |
| 303 | Methyl | OH | SO | Ethyl | |
| 304 | Methyl | OH | SO | Allyl | |
| 305 | Methyl | OH | S | (E)—2-Butenyl | |
| 306 | Methyl | OH | SO | (E)—3-Chloro—2-propenyl | |
| 307 | Methyl | OH | SO | Propargyl | |
| 308 | Methyl | OH | $SO_2$ | Ethyl | |
| 309 | Methyl | OH | $SO_2$ | Allyl | |
| 310 | Methyl | OH | $SO_2$ | (E)—2-Butenyl | |
| 311 | Methyl | OH | $SO_2$ | (E)—3-Chloro—2-propenyl | |
| 312 | Methyl | OH | $SO_2$ | Propargyl | |
| 313 | Methyl | Epoxy | S | Ethyl | |
| 314 | Methyl | Epoxy | S | Allyl | |
| 315 | Methyl | Epoxy | S | (E)—2-Butenyl | |
| 316 | Methyl | Epoxy | S | (E)—3-Chloro—2-propenyl | |
| 317 | Methyl | Epoxy | S | Propargyl | |
| 318 | Methyl | Epoxy | O | Ethyl | |
| 319 | Methyl | Epoxy | O | Allyl | |
| 320 | Methyl | Epoxy | O | (E)—2-Butenyl | |
| 321 | Methyl | Epoxy | O | (E)—3-Chloro—2-propenyl | |
| 322 | Methyl | Epoxy | O | Propargyl | |
| 323 | Methyl | Epoxy | SO | Ethyl | |
| 324 | Methyl | Epoxy | SO | Allyl | |
| 325 | Methyl | Epoxy | SO | (E)—2-Butenyl | |
| 326 | Methyl | Epoxy | SO | (E)—3-Chloro—2-propenyl | |
| 327 | Methyl | Epoxy | O | Propargyl | |
| 328 | Methyl | Epoxy | $SO_2$ | Ethyl | |
| 329 | Methyl | Epoxy | $SO_2$ | Allyl | |
| 330 | Methyl | Epoxy | $SO_2$ | (E)—2-Butenyl | |
| 331 | Methyl | Epoxy | $SO_2$ | (E)—3-Chloro—2-propenyl | |
| 332 | Methyl | Epoxy | $SO_2$ | Propargyl | |
| 333 | Ethyl | Cl | S | Ethyl | |
| 334 | Ethyl | Cl | S | Allyl | |
| 335 | Ethyl | Cl | S | (E)—2-Butenyl | |
| 336 | Ethyl | Cl | S | (E)—3-Chloro—2-propenyl | |
| 337 | Ethyl | Cl | S | Propargyl | |
| 338 | Ethyl | Cl | S | Ethyl | |
| 339 | Ethyl | Cl | O | Allyl | |
| 340 | Ethyl | Cl | O | (E)—2-Butenyl | |
| 341 | Ethyl | Cl | O | (E)—3-Chloro—2-propenyl | |
| 342 | Ethyl | Cl | O | Propargyl | |
| 343 | Ethyl | Cl | SO | Ethyl | |
| 344 | Ethyl | Cl | SO | Allyl | |
| 345 | Ethyl | Cl | SO | (E)—2-Butenyl | |
| 346 | Ethyl | Cl | SO | (E)—3-Chloro—2-propenyl | |
| 347 | Ethyl | Cl | O | Propargyl | |
| 348 | Ethyl | Cl | $SO_2$ | Ethyl | |
| 349 | Ethyl | Cl | $SO_2$ | Allyl | |
| 350 | Ethyl | Cl | $SO_2$ | (E)—2-Butenyl | |

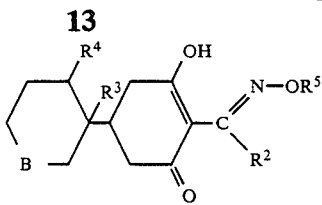

| No. | R² | R³ and R⁴ | B | R⁵ | ¹H—NMR data |
|---|---|---|---|---|---|
| 351 | Ethyl | Cl | SO₂ | (E)—3-Chloro—2-propenyl | |
| 352 | Ethyl | Cl | SO₂ | Propargyl | |
| 353 | Ethyl | Br | S | Ethyl | |
| 354 | Ethyl | Br | S | Allyl | |
| 355 | Ethyl | Br | S | (E)—2-Butenyl | |
| 356 | Ethyl | Br | S | (E)—3-Chloro—2-propenyl | |
| 357 | Ethyl | Br | S | Propargyl | |
| 358 | Ethyl | Br | O | Ethyl | |
| 359 | Ethyl | Br | O | Allyl | |
| 360 | Ethyl | Br | O | (E)—2-Butenyl | |
| 361 | Ethyl | Br | O | (E)—3-Chloro—2-propenyl | |
| 362 | Ethyl | Br | O | Propargyl | |
| 363 | Ethyl | Br | SO | Ethyl | |
| 364 | Ethyl | Br | SO | Allyl | |
| 365 | Ethyl | Br | SO | (E)—2-Butenyl | |
| 366 | Ethyl | Br | SO | (E)—3-Chloro—2-propenyl | |
| 367 | Ethyl | Br | SO | Propargyl | |
| 368 | Ethyl | Br | SO₂ | Ethyl | |
| 369 | Ethyl | Br | SO₂ | Allyl | |
| 370 | Ethyl | Br | SO₂ | (E)—2-Butenyl | |
| 371 | Ethyl | Br | SO₂ | (E)—3-Chloro—2-propenyl | |
| 372 | Ethyl | Br | SO₂ | Propargyl | |
| 373 | Ethyl | OH | S | Ethyl | |
| 374 | Ethyl | OH | S | Allyl | |
| 375 | Ethyl | OH | S | (E)—2-Butenyl | |
| 376 | Ethyl | OH | S | (E)—3-Chloro—2-propenyl | |
| 377 | Ethyl | OH | S | Propargyl | |
| 378 | Ethyl | OH | O | Ethyl | |
| 379 | Ethyl | OH | O | Allyl | |
| 380 | Ethyl | OH | O | (E)—2-Butenyl | |
| 381 | Ethyl | OH | O | (E)—3-Chloro—2-propenyl | |
| 382 | Ethyl | OH | O | Propargyl | |
| 383 | Ethyl | OH | SO | Ethyl | |
| 384 | Ethyl | OH | SO | Allyl | |
| 385 | Ethyl | OH | SO | (E)—2-Butenyl | |
| 386 | Ethyl | OH | SO | (E)—3-Chloro—2-propenyl | |
| 387 | Ethyl | OH | SO | Propargyl | |
| 388 | Ethyl | OH | SO₂ | Ethyl | |
| 389 | Ethyl | OH | SO₂ | Allyl | |
| 390 | Ethyl | OH | SO₂ | (E)—2-Butenyl | |
| 391 | Ethyl | OH | SO₂ | (E)—3-Chloro—2-propenyl | |
| 392 | Ethyl | OH | SO₂ | Propargyl | |
| 393 | Ethyl | Epoxy | S | Ethyl | |
| 394 | Ethyl | Epoxy | S | Allyl | |
| 395 | Ethyl | Epoxy | S | (E)—2-Butenyl | |
| 396 | Ethyl | Epoxy | S | (E)—3-Chloro—2-propenyl | |
| 397 | Ethyl | Epoxy | S | Propargyl | |
| 398 | Ethyl | Epoxy | O | Ethyl | 1.3(t), 2.5(m), 3.3(s) |
| 399 | Ethyl | Epoxy | O | Allyl | 1.3(t), 3.5(m), 4.6(d) |
| 400 | Ethyl | Epoxy | O | (E)—2-Butenyl | |
| 401 | Ethyl | Epoxy | O | (E)—3-Chloro—2-propenyl | 2.0(m), 3.5(m), 6.35(d) |
| 402 | Ethyl | Epoxy | O | Propargyl | |
| 403 | Ethyl | Epoxy | SO | Ethyl | |
| 404 | Ethyl | Epoxy | SO | Allyl | |
| 405 | Ethyl | Epoxy | SO | (E)—2-Butenyl | |
| 406 | Ethyl | Epoxy | SO | (E)—3-Chloro—2-propenyl | |
| 407 | Ethyl | Epoxy | SO | Propargyl | |
| 408 | Ethyl | Epoxy | SO₂ | Ethyl | |
| 409 | Ethyl | Epoxy | SO₂ | Allyl | |
| 410 | Ethyl | Epoxy | SO₂ | (E)—2-Butenyl | |
| 411 | Ethyl | Epoxy | SO₂ | (E)—3-Chloro—2-propenyl | |
| 412 | Ethyl | Epoxy | SO₂ | Propargyl | |
| 413 | n-Propyl | Cl | S | Ethyl | |
| 414 | n-Propyl | Cl | S | Allyl | |
| 415 | n-Propyl | Cl | S | (E)—2-Butenyl | |
| 416 | n-Propyl | Cl | S | (E)—3-Chloro—2-propenyl | |
| 417 | n-Propyl | Cl | S | Propargyl | |
| 418 | n-Propyl | Cl | O | Ethyl | 1.3(t), 1.6(q), 4.4(s) |
| 419 | n-Propyl | Cl | O | Allyl | |
| 420 | n-Propyl | Cl | O | (E)—2-Butenyl | |
| 421 | n-Propyl | Cl | O | (E)—3-Chloro—2-propenyl | 1.0(t), 3.9(m), 4.5(d) |
| 422 | n-Propyl | Cl | O | Propargyl | |
| 423 | n-Propyl | Cl | SO | Ethyl | |
| 424 | n-Propyl | Cl | SO | Allyl | |

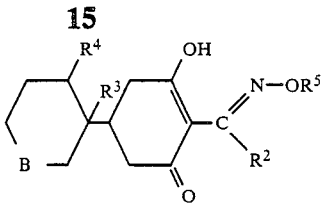

| No. | R² | R³ and R⁴ | B | R⁵ | ¹H—NMR data |
|---|---|---|---|---|---|
| 425 | n-Propyl | Cl | SO | (E)—2-Butenyl | |
| 426 | n-Propyl | Cl | SO | (E)—3-Chloro—2-propenyl | |
| 427 | n-Propyl | Cl | SO | Propargyl | |
| 428 | n-Propyl | Cl | SO₂ | Ethyl | |
| 429 | n-Propyl | Cl | SO₂ | Allyl | |
| 430 | n-Propyl | Cl | SO₂ | (E)—2-Butenyl | |
| 431 | n-Propyl | Cl | SO₂ | (E)—3-Chloro—2-propenyl | |
| 432 | n-Propyl | Cl | SO₂ | Propargyl | |
| 433 | n-Propyl | Br | S | Ethyl | |
| 434 | n-Propyl | Br | S | Allyl | |
| 435 | n-Propyl | Br | S | (E)—2-Butenyl | |
| 436 | n-Propyl | Br | S | (E)—3-Chloro—2-propenyl | |
| 437 | n-Propyl | Br | S | Propargyl | |
| 438 | n-Propyl | Br | O | Ethyl | 1.3(t), 3.9(m), 4.65(s) |
| 439 | n-Propyl | Br | O | Allyl | 1.9(d), 4.5(d), 4.6(s) |
| 440 | n-Propyl | Br | O | (E)—2-Butenyl | 0.95(t), 1.8(d), 4.6(s) |
| 441 | n-Propyl | Br | O | (E)—3-Chloro—2-propenyl | 0.95(t), 1.5(q), 6.3(d) |
| 442 | n-Propyl | Br | O | Propargyl | |
| 443 | n-Propyl | Br | SO | Ethyl | |
| 444 | n-Propyl | Br | SO | Allyl | |
| 445 | n-Propyl | Br | SO | (E)—2-Butenyl | |
| 446 | n-Propyl | Br | SO | (E)—3-Chloro—2-propenyl | |
| 447 | n-Propyl | Br | SO | Propargyl | |
| 448 | n-Propyl | Br | SO₂ | Ethyl | |
| 449 | n-Propyl | Br | SO₂ | Allyl | |
| 450 | n-Propyl | Br | SO₂ | (E)—2-Butenyl | |
| 451 | n-Propyl | Br | SO₂ | (E)—3-Chloro—2-propenyl | |
| 452 | n-Propyl | Br | SO₂ | Propargyl | |
| 453 | n-Propyl | OH | S | Ethyl | |
| 454 | n-Propyl | OH | S | Allyl | |
| 455 | n-Propyl | OH | S | (E)—2-Butenyl | |
| 456 | n-Propyl | OH | S | (E)—3-Chloro—2-propenyl | |
| 457 | n-Propyl | OH | S | Propargyl | |
| 458 | n-Propyl | OH | O | Ethyl | 1.0(t), 2.6(m), 4.1(q) |
| 459 | n-Propyl | OH | O | Allyl | |
| 460 | n-Propyl | OH | O | (E)—2-Butenyl | |
| 461 | n-Propyl | OH | O | (E)—3-Chloro—2-propenyl | |
| 462 | n-Propyl | OH | O | Propargyl | |
| 463 | n-Propyl | OH | SO | Ethyl | |
| 464 | n-Propyl | OH | SO | Allyl | |
| 465 | n-Propyl | OH | SO | (E)—2-Butenyl | |
| 466 | n-Propyl | OH | SO | (E)—3-Chloro—2-propenyl | |
| 467 | n-Propyl | OH | SO | Propargyl | |
| 468 | n-Propyl | OH | SO₂ | Ethyl | |
| 469 | n-Propyl | OH | SO₂ | Allyl | |
| 470 | n-Propyl | OH | SO₂ | (E)—2-Butenyl | |
| 471 | n-Propyl | OH | SO₂ | (E)—3-Chloro—2-propenyl | |
| 472 | n-Propyl | OH | SO₂ | Propargyl | |
| 473 | n-Propyl | Epoxy | S | Ethyl | |
| 474 | n-Propyl | Epoxy | S | Allyl | |
| 475 | n-Propyl | Epoxy | S | (E)—2-Butenyl | |
| 476 | n-Propyl | Epoxy | S | (E)—3-Chloro—2-propenyl | |
| 477 | n-Propyl | Epoxy | S | Propargyl | |
| 478 | n-Propyl | Epoxy | O | Ethyl | 1.35(t), 2.0(m), 3.3(s) |
| 479 | n-Propyl | Epoxy | O | Allyl | |
| 480 | n-Propyl | Epoxy | O | (E)—2-Butenyl | 0.95(t), 1.5(m), 3.3(s) |
| 481 | n-Propyl | Epoxy | O | (E)—3-Chloro—2-propenyl | |
| 482 | n-Propyl | Epoxy | O | Propargyl | |
| 483 | n-Propyl | Epoxy | SO | Ethyl | |
| 484 | n-Propyl | Epoxy | SO | Allyl | |
| 485 | n-Propyl | Epoxy | SO | (E)—2-Butenyl | |
| 486 | n-Propyl | Epoxy | SO | (E)—3-Chloro—2-propenyl | |
| 487 | n-Propyl | Epoxy | SO | Propargyl | |
| 488 | n-Propyl | Epoxy | SO₂ | Ethyl | |
| 489 | n-Propyl | Epoxy | SO₂ | Allyl | |
| 490 | n-Propyl | Epoxy | SO₂ | (E)—2-Butenyl | |
| 491 | n-Propyl | Epoxy | SO₂ | (E)—3-Chloro—2-propenyl | |
| 492 | n-Propyl | Epoxy | SO₂ | Propargyl | |
| 493 | n-Butyl | Cl | S | Ethyl | |
| 494 | n-Butyl | Cl | S | Allyl | |
| 495 | n-Butyl | Cl | S | (E)—2-Butenyl | |
| 496 | n-Butyl | Cl | S | (E)—3-Chloro—2-propenyl | |
| 497 | n-Butyl | Cl | S | Propargyl | |
| 498 | n-Butyl | Cl | O | Ethyl | |

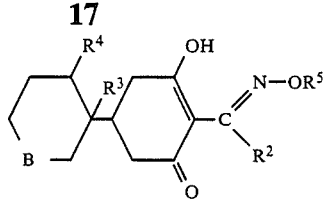

| No. | $R^2$ | $R^3$ and $R^4$ | B | $R^5$ | $^1$H—NMR data |
|---|---|---|---|---|---|
| 499 | n-Butyl | Cl | O | Allyl | |
| 500 | n-Butyl | Cl | O | (E)—2-Butenyl | |
| 501 | n-Butyl | Cl | O | (E)—3-Chloro—2-propenyl | |
| 502 | n-Butyl | Cl | O | Propargyl | |
| 503 | n-Butyl | Cl | SO | Ethyl | |
| 504 | n-Butyl | Cl | SO | Allyl | |
| 505 | n-Butyl | Cl | SO | (E)—2-Butenyl | |
| 506 | n-Butyl | Cl | SO | (E)—3-Chloro—2-propenyl | |
| 507 | n-Butyl | Cl | SO | Propargyl | |
| 508 | n-Butyl | Cl | $SO_2$ | Ethyl | |
| 509 | n-Butyl | Cl | $SO_2$ | Allyl | |
| 510 | n-Butyl | Cl | $SO_2$ | (E)—2-Butenyl | |
| 511 | n-Butyl | Cl | $SO_2$ | (E)—3-Chloro—2-propenyl | |
| 512 | n-Butyl | Cl | $SO_2$ | Propargyl | |
| 513 | n-Butyl | Br | S | Ethyl | |
| 514 | n-Butyl | Br | S | Allyl | |
| 515 | n-Butyl | Br | S | (E)—2-Butenyl | |
| 516 | n-Butyl | Br | S | (E)—3-Chloro—2-propenyl | |
| 517 | n-Butyl | Br | S | Propargyl | |
| 518 | n-Butyl | Br | O | Ethyl | |
| 519 | n-Butyl | Br | O | Allyl | |
| 520 | n-Butyl | Br | O | (E)—2-Butenyl | |
| 521 | n-Butyl | Br | O | (E)—3-Chloro—2-propenyl | |
| 522 | n-Butyl | Br | O | Propargyl | |
| 523 | n-Butyl | Br | SO | Ethyl | |
| 524 | n-Butyl | Br | SO | Allyl | |
| 525 | n-Butyl | Br | SO | (E)—2-Butenyl | |
| 526 | n-Butyl | Br | SO | (E)—3-Chloro—2-propenyl | |
| 527 | n-Butyl | Br | SO | Propargyl | |
| 528 | n-Butyl | Br | $SO_2$ | Ethyl | |
| 529 | n-Butyl | Br | $SO_2$ | Allyl | |
| 530 | n-Butyl | Br | $SO_2$ | (E)—2-Butenyl | |
| 531 | n-Butyl | Br | $SO_2$ | (E)—3-Chloro—2-propenyl | |
| 532 | n-Butyl | Br | $SO_2$ | Propargyl | |
| 533 | n-Butyl | OH | S | Ethyl | |
| 534 | n-Butyl | OH | S | Allyl | |
| 535 | n-Butyl | OH | S | (E)—2-Butenyl | |
| 536 | n-Butyl | OH | S | (E)—3-Chloro—2-propenyl | |
| 537 | n-Butyl | OH | S | Propargyl | |
| 538 | n-Butyl | OH | O | Ethyl | |
| 539 | n-Butyl | OH | O | Allyl | |
| 540 | n-Butyl | OH | O | (E)—2-Butenyl | |
| 541 | n-Butyl | OH | O | (E)—3-Chloro—2-propenyl | |
| 542 | n-Butyl | OH | O | Propargyl | |
| 543 | n-Butyl | OH | SO | Ethyl | |
| 544 | n-Butyl | OH | SO | Allyl | |
| 545 | n-Butyl | OH | SO | (E)—2-Butenyl | |
| 546 | n-Butyl | OH | SO | (E)—3-Chloro—2-propenyl | |
| 547 | n-Butyl | OH | SO | Propargyl | |
| 548 | n-Butyl | OH | $SO_2$ | Ethyl | |
| 549 | n-Butyl | OH | $SO_2$ | Allyl | |
| 550 | n-Butyl | OH | $SO_2$ | (E)—2-Butenyl | |
| 551 | n-Butyl | OH | $SO_2$ | (E)—3-Chloro—2-propenyl | |
| 552 | n-Butyl | OH | $SO_2$ | Propargyl | |
| 553 | n-Butyl | Epoxy | S | Ethyl | |
| 554 | n-Butyl | Epoxy | S | Allyl | |
| 555 | n-Butyl | Epoxy | S | (E)—2-Butenyl | |
| 556 | n-Butyl | Epoxy | S | (E)—3-Chloro—2-propenyl | |
| 557 | n-Butyl | Epoxy | S | Propargyl | |
| 558 | n-Butyl | Epoxy | O | Ethyl | |
| 559 | n-Butyl | Epoxy | O | Allyl | |
| 560 | n-Butyl | Epoxy | O | (E)—2-Butenyl | |
| 561 | n-Butyl | Epoxy | O | (E)—3-Chloro—2-propenyl | |
| 562 | n-Butyl | Epoxy | O | Propargyl | |
| 563 | n-Butyl | Epoxy | SO | Ethyl | |
| 564 | n-Butyl | Epoxy | SO | Allyl | |
| 565 | n-Butyl | Epoxy | SO | (E)—2-Butenyl | |
| 566 | n-Butyl | Epoxy | SO | (E)—3-Chloro—2-propenyl | |
| 567 | n-Butyl | Epoxy | SO | Propargyl | |
| 568 | n-Butyl | Epoxy | $SO_2$ | Ethyl | |
| 569 | n-Butyl | Epoxy | $SO_2$ | Allyl | |
| 570 | n-Butyl | Epoxy | $SO_2$ | (E)—2-Butenyl | |
| 571 | n-Butyl | Epoxy | $SO_2$ | (E)—3-Chloro—2-propenyl | |

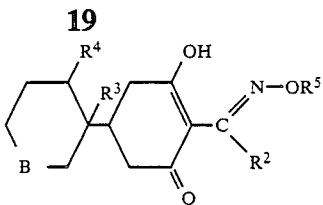

| No. | R² | R³ and R⁴ | B | R⁵ | ¹H—NMR data |
|---|---|---|---|---|---|
| 572 | n-Butyl | Epoxy | SO₂ | Propargyl | |

TABLE 5

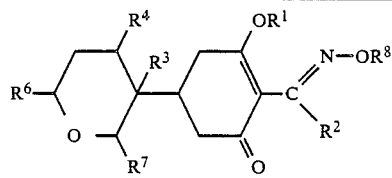

| No. | R¹ | R² | R³ | R⁴ | R⁶ and R⁷ | R⁸ | ¹H—NMR data |
|---|---|---|---|---|---|---|---|
| 573 | H | n-Propyl | OH | Dimethylamino | H | Ethyl | |
| 574 | H | n-Propyl | OH | Methylthio | H | Ethyl | |
| 575 | H | n-Propyl | OH | Ethylthio | H | Ethyl | |
| 576 | H | n-Propyl | OH | Thiocarbonylmethyl | H | Ethyl | |
| 577 | H | n-Propal | OH | Thiomethylcarboxyl | H | Ethyl | |
| 578 | H | n-Propyl | H | Methylthio | H | Ethyl | |
| 579 | H | n-Propyl | H | Ethylthio | H | Ethyl | |
| 580 | H | n-Propyl | H | Thiocarbonylmethyl | H | Ethyl | |
| 581 | H | n-Propyl | H | Thiomethylcarbonyl | H | Ethyl | |
| 582 | Benzoyl | n-Propyl | OH | Methylthio | H | Ethyl | |
| 583 | H | Ethyl | H | Thiocarbonylmethyl | H | Ethyl | |
| 584 | H | Ethyl | H | Thiocarbonylmethyl | H | Allyl | |
| 585 | H | Ethyl | H | Thiocarbonylmethyl | H | Propargyl | |
| 586 | H | Methyl | H | Thiocarbonylmethyl | H | Ethyl | |
| 587 | H | Methyl | H | Thiocarbonylmethyl | H | Allyl | |
| 588 | Benzoyl | n-Propyl | R³ and R⁴ = Epoxy | | H | Ethyl | |
| 589 | Stearoyl | n-Propyl | R³ and R⁴ = Epoxy | | H | Ethyl | |
| 590 | H | n-Propyl | Methylthio | OH | Methyl | Ethyl | |
| 591 | H | n-Propyl | Ethylthio | OH | Methyl | Ethyl | |
| 672 | H | n-Propyl | R³ and R⁴ = Epoxy | | Methyl | Ethyl | 0.96(t), 3.91(q), 4.09(q) |

TABLE 6

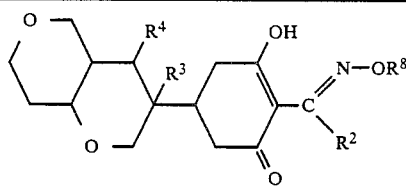

TABLE 6-continued

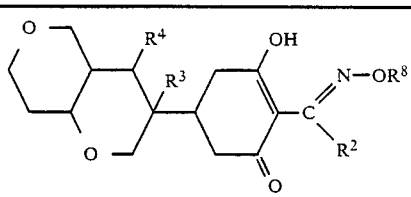

| No. | R² | R³ and R⁴ | R⁸ | ¹H—NMR data | No. | R² | R³ and R⁴ | R⁸ | ¹H—NMR data |
|---|---|---|---|---|---|---|---|---|---|
| 592 | Methyl | Cl | Ethyl | | 614 | Ethyl | Cl | (E)-2-Butenyl | |
| 593 | Methyl | Cl | Allyl | | 615 | Ethyl | Cl | (E)-3-Chloro-2-propenyl | |
| 594 | Methyl | Cl | (E)-2-Butenyl | | 616 | Ethyl | Cl | Propargyl | |
| 595 | Methyl | Cl | (E)-3-Chloro-2-propenyl | | 617 | Ethyl | Br | Ethyl | |
| 596 | Methyl | Cl | Propargyl | | 618 | Ethyl | Br | Allyl | |
| 597 | Methyl | Br | Ethyl | | 619 | Ethyl | Br | (E)-2-Butenyl | |
| 598 | Methyl | Br | Allyl | | 620 | Ethyl | Br | (E)-3-Chloro-2-propenyl | |
| 599 | Methyl | Br | (E)-2-Butenyl | | 621 | Ethyl | Br | Propargyl | |
| 600 | Methyl | Br | (E)-3-Chloro-2-propenyl | | 622 | Ethyl | OH | Ethyl | |
| 601 | Methyl | Br | Propargyl | | 623 | Ethyl | OH | Allyl | |
| 602 | Methyl | OH | Ethyl | | 624 | Ethyl | OH | (E)-2-Butenyl | |
| 603 | Methyl | OH | Allyl | | 625 | Ethyl | OH | (E)-3-Chloro-2-propenyl | |
| 604 | Methyl | OH | (E)-2-Butenyl | | 626 | Ethyl | OH | Propargyl | |
| 605 | Methyl | OH | (E)-3-Chloro-2-propenyl | | 627 | Ethyl | Epoxy | Ethyl | |
| 606 | Methyl | OH | Propargyl | | 628 | Ethyl | Epoxy | Allyl | |
| 607 | Methyl | Epoxy | Ethyl | | 629 | Ethyl | Epoxy | (E)-2-Butenyl | |
| 608 | Methyl | Epoxy | Allyl | | 630 | Ethyl | Epoxy | (E)-3-Chloro-2-propenyl | |
| 609 | Methyl | Epoxy | (E)-2-Butenyl | | 631 | Ethyl | Epoxy | Propargyl | |
| 610 | Methyl | Epoxy | (E)-3-Chloro-2-propenyl | | 632 | n-Propyl | Cl | Ethyl | |
| 611 | Methyl | Epoxy | Propargyl | | 633 | n-Propyl | Cl | Allyl | |
| 612 | Ethyl | Cl | Ethyl | | 634 | n-Propyl | Cl | (E)-2-Butenyl | |
| 613 | Ethyl | Cl | Allyl | | 635 | n-Propyl | Cl | (E)-3-Chloro-2-propenyl | |

TABLE 6-continued

[Structure: cyclohexenone derivative with R³, R⁴, OH, N—OR⁸, R², and dioxane substituents]

| No. | R² | R³ and R⁴ | R⁸ | ¹H—NMR data |
|---|---|---|---|---|
| 636 | n-Propyl | Cl | Propargyl | |
| 637 | n-Propyl | Br | Ethyl | 1.6(q), 2.6(m), 4.1(q) |
| 638 | n-Propyl | Br | Allyl | 1.0(t), 3.9(m), 5.4(m) |
| 639 | n-Propyl | Br | (E)-2-Butenyl | 1.0(t), 1.7(d), 2.9(m) |
| 640 | n-Propyl | Br | (E)-3-Chloro-2-propenyl | 1.5(q), 2.9(t), 4.0(s) |
| 641 | n-Propyl | Br | Propargyl | |
| 642 | n-Propyl | OH | Ethyl | |
| 643 | n-Propyl | OH | Allyl | |
| 644 | n-Propyl | OH | (E)-2-Butenyl | |
| 645 | n-Propyl | OH | (E)-3-Chloro-2-propenyl | |
| 646 | n-Propyl | OH | Propargyl | |
| 647 | n-Propyl | Epoxy | Ethyl | 1.3(t), 2.3(m), 3.1(s) |
| 648 | n-Propyl | Epoxy | Allyl | 0.95(t), 3.1(s), 4.5(d) |
| 649 | n-Propyl | Epoxy | (E)-2-Butenyl | |
| 650 | n-Propyl | Epoxy | (E)-3-Chloro-2-propenyl | 1.35(t), 2.0(m), 3.3(s) |
| 651 | n-Propyl | Epoxy | Propargyl | |
| 652 | n-Butyl | Cl | Ethyl | |
| 653 | n-Butyl | Cl | Allyl | |
| 654 | n-Butyl | Cl | (E)-2-Butenyl | |
| 655 | n-Butyl | Cl | (E)-3-Chloro-2-propenyl | |
| 656 | n-Butyl | Cl | Propargyl | |
| 657 | n-Butyl | Br | Ethyl | |
| 658 | n-Butyl | Br | Allyl | |
| 659 | n-Butyl | Br | (E)-2-Butenyl | |
| 660 | n-Butyl | Br | (E)-3-Chloro-2-propenyl | |
| 661 | n-Butyl | Br | Propargyl | |
| 662 | n-Butyl | OH | Ethyl | |
| 663 | n-Butyl | OH | Allyl | |
| 664 | n-Butyl | OH | (E)-2-Butenyl | |
| 665 | n-Butyl | OH | (E)-3-Chloro-2-propenyl | |
| 666 | n-Butyl | OH | Propargyl | |
| 667 | n-Butyl | Epoxy | Ethyl | |
| 668 | n-Butyl | Epoxy | Allyl | |
| 669 | n-Butyl | Epoxy | (E)-2-Butenyl | |
| 670 | n-Butyl | Epoxy | (E)-3-Chloro-2-propenyl | |
| 671 | n-Butyl | Epoxy | Propargyl | |

TABLE 7

| No. | A | B | X | R¹ | R² | R³ R⁴ | R⁵ | R⁶ | R⁷ | R⁸ | |
|---|---|---|---|---|---|---|---|---|---|---|---|
| 673 | NOR⁸ | O | H | C₃H₇CO | Propyl | —O— | —CH₂OC₂H₄— | H | Ethyl | 0.90(t), 1.0(t), 1.24(t) | |
| 674 | NOR⁸ | O | H | Benzoyl | Propyl | —O— | —CH₂OC₂H₄— | H | Ethyl | 0.86(t), 1.09(t), 7.3–8.2(m) | |
| 675 | NOR⁸ | O | H | Acetyl | Propyl | —O— | —CH₂OC₂H₄— | H | Ethyl | 0.88(t), 1.25(t), 2.19(s) | |

The cyclohexenone derivatives of the formula I, and their salts, may be applied for instance in the form of directly sprayable solutions, powders, suspensions (including high-percentage aqueous, oily or other suspensions), dispersions, emulsions, oil dispersions, pastes, dusts, broadcasting agents or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, and paraffin, tetrahydrocarbons such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensation products of sulfonated naphthalene and naphthalene derivatives with formaldehyde, condensation products of naphthalene or naphthalenesulfonic acids with phenol or formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate and ureas, and vegetable products such as grain flours, bark meal, wood meal and nutshell meal, cellulosic powders, etc.

The formulations contain from 0.1 to 95, and preferably from 0.5 to 90, % by weight of active ingredient.

Examples of formulations are given below.

I. 90 parts by weight of compound no. 647 is mixed with 10 parts by weight of N-methyl-α-pyrrolidone. A mixture is obtained which is suitable for application in the form of very fine drops.

II. 20 parts by weight of compound no. 648 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of active ingredient.

III. 20 parts by weight of compound no. 650 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of active ingredient.

IV. 20 parts by weight of compound no. 637 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of active ingredient.

V. 20 parts by weight of compound no. 638 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of active ingredient.

VI. 3 parts by weight of compound no. 640 is intimately mixed with 97 parts by weight of particulate kaolin. A dust is obtained containing 3% by weight of active ingredient.

VII. 30 parts by weight of compound no. 478 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 480 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

IX. 10 parts by weight of compound no. 440 is mixed with 90 parts by weight of a mixture consisting of 93 parts by weight of xylene and 7 parts by weight of the adduct of 8 moles of ethylene oxide and 1 mole of nonylphenol. A solution is obtained containing 10 wt% of the active ingredient.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amounts of active ingredient applied depends on the time of the year, the plants to be combated and their growth stage, and varies from 0.01 to 3 kg/ha, but is preferably from 0.05 to 0.5 kg/ha.

The action of the cyclohexenone derivatives of the formula I on plant growth is demonstrated in greenhouse experiments.

The vessels employed were plastic flowerpots having a volume of 300 cm$^3$, and which were filled with a sandy loam containing about 3.0% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. The application rate for postemergence treatment was 0.125 kg of active ingredient per hectare. No covers were placed on the vessels in this method.

The pots were set up in the greenhouse—species from warmer areas at from 20° C. to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Alopecurus myosuroides, Avena fatua, Avena sativa, Digitaria sanguinalis, Echinochloa crus-galli, Lolium multiflorum, Medicago sativa, Setaria italica, Sinapis alba, Sorghum halepense, Triticum aestivum,* and *Zea mays.*

Grasses from the Gramineae family were well combated with a preemergence application of 3.0 kg/ha of, for example, compounds 647, 648, 650, 637, 638, 640, 478, 480 and 440. Sinapis alba (broadleaved crop plant) suffered no damage whatsoever.

Compounds 647, 648, 650 and 401 are suitable, at a rate of 0.125 kg/ha, for controlling, postemergence, a broad spectrum of unwanted grassy plants. Volunteer crop plants from the Gramineae family are also combated. Alfalfa—a broadleaved crop plant—remain completely uninfluenced.

Unwanted grassy species are well combated by postemergence applications of active ingredients 438, 439 and 674; wheat remains unaffected.

In view of the spectrum of weeds which can be combated, the tolerance of the active ingredients according to the invention by crop plants, the desired influence on the growth of crop plants, and in view of the numerous application methods possible, the compounds according to the invention may be used in a large number of crop plants.

The following crops may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | bermudagrass |
| Daucus carota | carrots |
| Elaeis guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactua sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |

| Botanical name | Common name |
| --- | --- |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenone derivatives of the formula I may be mixed and applied together with numerous representatives of other herbicidal or growth-regulating active ingredient groups. Examples or suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acid derivatives, etc.

It may also be useful to apply the compounds of the formula I, or herbicidal agents containing them, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenone derivative of the formula

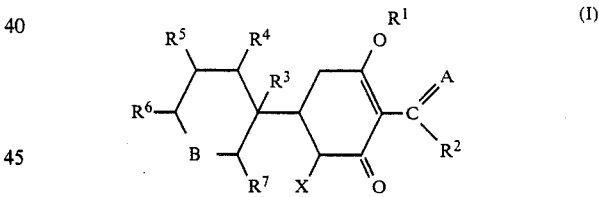

where

A is oxygen or $NOR^8$, where $R^8$ is alkyl of 1 to 4 carbon atoms, alkenyl of 3 or 4 carbon atoms, alkynyl of 3 or 4 carbon atoms, haloalkyl or haloalkenyl of 2 to 4 carbon atoms and 1 to 3 halogen atoms, chlorothienyl or alkoxyalkyl of 2 to 4 carbon atoms, B is O, X is hydrogen or methoxycarbonyl, $R^1$ is hydrogen, carbonylalkyl of 2 to 18 carbon atoms or benzoyl or an inorganic or organic cation, $R^2$ is alkyl of up to 4 carbon atoms, $R^3$ and $R^4$, independently of each other, are each hydroxyl, chlorine, bromine, thioalkylcarboxyl, thiocarbonylalkyl, alkylcarbonyloxy each of up to 4 carbon atoms or $R^3$ and $R^4$ are together alkoxy of up to 3 carbon atoms and hydroxyl or together alkylthio of up to 3 carbon atoms and hydroxyl or together form an epoxy group, $R^5$ and $R^6$, independently of each other, are each hydrogen or methyl or $R^5$ and $R^6$ together form a methyleneoxyethylene group, and $R^7$ is hydrogen or methyl.

2. A cyclohexenone derivative as set forth in claim 1, where A is $NOR^8$, B is oxygen, X is hydrogen, $R^1$ is hydrogen, $R^2$ is ethyl or propyl, each of $R^3$ and $R^4$ is bromine or $R^3$ and $R^4$ together are an epoxy group, each of $R^5$ and $R^6$ is hydrogen or $R^5$ and $R^6$ together are a methyleneoxyethylene group, $R^7$ is hydrogen, and $R^8$ is ethyl, allyl, chloropropenyl or butenyl.

3. The cyclohexenone derivative of the formula I as defined in claim 1 which is 2-(1-((E)-2-butenyloxyimino)butyl)-5-(1,6-dibromo-tetrahydropyran-3-yl)-3-hydroxy-2-cyclohexen-1-one.

4. A herbicide containing an inert additive and an effective amount of a compound of the formula

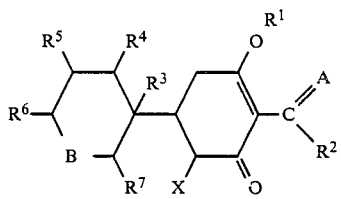
(I)

where

A is oxygen or $NOR^8$, where $R^8$ is alkyl of 1 to 4 carbon atoms, alkenyl of 3 or 4 carbon atoms, alkynyl of 3 or 4 carbon atoms, haloalkyl or haloalkenyl of 2 to 4 carbon atoms and 1 to 3 halogen atoms, chlorothienyl or alkoxyalkyl of 2 to 4 carbon atoms, B is O, X is hydrogen or methoxycarbonyl, $R^1$ is hydrogen, carbonylalkyl of 2 to 18 carbon atoms or benzoyl or an inorganic or organic cation, $R^2$ is alkyl of up to 4 carbon atoms, $R^3$ and $R^4$, independently of each other, are each hydroxyl, chlorine, bromine, thioalkylcarboxyl, thiocarbonylalkyl, alkylcarbonyloxy each of up to 4 carbon atoms or $R^3$ and $R^4$ are together alkoxy of up to 3 carbon atoms and hydroxyl or together alkylthio of up to 3 carbon atoms and hydroxyl or together form an epoxy group, $R^5$ and $R^6$, independently of each other, are each hydrogen or methyl or $R^5$ and $R^6$ together form a methyleneoxyethylene group, and $R^7$ is hydrogen or methyl.

5. A herbicide as set forth in claim 4 containing an effective amount of a compound of the formula I, where A is $NOR^8$, B is oxygen, X is hydrogen, $R^1$ is hydrogen, $R^2$ is ethyl or propyl, each of $R^3$ and $R^4$ is bromine or $R^3$ and $R^4$ together are an epoxy group, $R^5$ and $R^6$ are each hydrogen or $R^5$ and $R^6$ together are a methyleneoxyethylene group, $R^7$ is hydrogen, and $R^8$ is ethyl, allyl, chloropropenyl or butenyl.

6. A process for combating the growth of unwanted plants, wherein the unwanted plants or the area to be kept free from unwanted plant growth are treated with a herbicidally effective amount of a compound of the formula

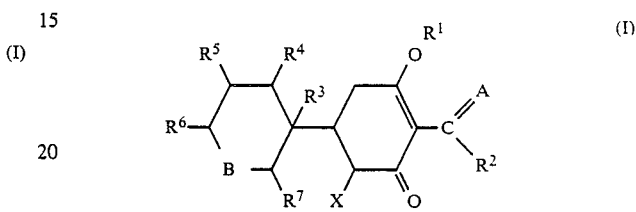
(I)

where

A is oxygen or $NOR^8$, where $R^8$ is alkyl of 1 to 4 carbon atoms, alkenyl of 3 or 4 carbon atoms, alkynyl of 3 or 4 carbon atoms, haloalkyl or haloalkenyl of 2 to 4 carbon atoms and 1 to 3 halogen atoms, chlorothienyl or alkoxyalkyl of 2 to 4 carbon atoms, B is O, X is hydrogen or methoxycarbonyl, $R^1$ is hydrogen, carbonylalkyl of 2 to 18 carbon atoms or benzoyl or an inorganic or organic cation, $R^2$ is alkyl of up to 4 carbon atoms, $R^3$ and $R^4$, independently of each other, are each hydroxyl, chlorine, bromine, thioalkylcarboxyl, thiocarbonylalkyl, alkylcarbonyloxy each of up to 4 carbon atoms or $R^3$ and $R^4$ are together alkoxy of up to 3 carbon atoms and hydroxyl or together alkylthio of up to 3 carbon atoms and hydroxyl or together form an epoxy group, $R^5$ and $R^6$, independently of each other, are each hydrogen or methyl or $R^5$ and $R^6$ together form a methyleneoxyethylene group, and $R^7$ is hydrogen or methyl.

* * * * *